(12) United States Patent
Deng

(10) Patent No.: US 7,237,990 B2
(45) Date of Patent: Jul. 3, 2007

(54) SURGICAL TOOL SYSTEM WITH QUICK RELEASE COUPLING ASSEMBLY

(75) Inventor: Wenjie Deng, San Jose, CA (US)

(73) Assignee: Stryker Corporation, Kalamazoo, MI (US)

( * ) Notice: Subject to any disclaimer, the term of this patent is extended or adjusted under 35 U.S.C. 154(b) by 662 days.

(21) Appl. No.: 10/319,300

(22) Filed: Dec. 13, 2002

(65) Prior Publication Data

US 2004/0092991 A1    May 13, 2004

Related U.S. Application Data

(63) Continuation-in-part of application No. 10/214,937, filed on Aug. 8, 2002.

(51) Int. Cl.
*B23C 1/20* (2006.01)

(52) U.S. Cl. .................. 409/175; 409/182; 279/79; 279/84

(58) Field of Classification Search ............... 409/175, 409/182; 279/79, 84
See application file for complete search history.

(56) References Cited

U.S. PATENT DOCUMENTS

| | | | |
|---|---|---|---|
| 4,355,977 A | | 10/1982 | Ota et al. |
| 4,588,335 A | * | 5/1986 | Pearson, Jr. ............ 408/239 R |
| 4,605,348 A | * | 8/1986 | DeCaro ................. 408/239 A |
| 4,705,038 A | | 11/1987 | Sjostrom et al. |
| 4,887,929 A | * | 12/1989 | Hale ....................... 403/328 |
| 5,176,143 A | | 1/1993 | Eckerle et al. ............ 600/490 |
| 5,192,292 A | | 3/1993 | Cezana et al. |
| 5,400,267 A | | 3/1995 | Denen et al. |
| 5,443,082 A | | 8/1995 | Mewburn |
| 5,460,490 A | | 10/1995 | Carr et al. |
| 5,628,731 A | | 5/1997 | Dodge et al. |
| 5,632,759 A | | 5/1997 | Rexroth ................. 606/180 |
| 5,747,953 A | | 5/1998 | Philipp |

(Continued)

FOREIGN PATENT DOCUMENTS

DE    39 17 876    12/1990

(Continued)

OTHER PUBLICATIONS

U.S. Appl. No. 10/210,325, filed Aug. 1, 2002.

(Continued)

*Primary Examiner*—Monica Carter
*Assistant Examiner*—Eric A. Gates
(74) *Attorney, Agent, or Firm*—Flynn, Thiel, Boutell & Tanis, P.C.

(57) ABSTRACT

A surgical tool system with a handpiece and a cutting accessory that has inner and outer hubs. The handpiece has a spring biased lock ring that abuts a complementary stop member integral with the accessory outer hub to hold the accessory to the handpiece. An RFID chip is disposed against an inner wall of the accessory outer hub. An elastomeric seal pressed against the inner wall of the accessory outer hub provides environmental protection for the RFID chip. The seal has a rib that extends around the outer perimeter of the proximal end of the outer hub so as to form a seal between the accessory and an adjacent inner wall of the handpiece. Stop tabs extend inwardly from the seal to prevent the drive hub disposed inside the outer hub from falling out.

27 Claims, 8 Drawing Sheets

U.S. PATENT DOCUMENTS

| | | |
|---|---|---|
| 5,810,770 A | 9/1998 | Chin et al. |
| 6,017,354 A | 1/2000 | Culp et al. |
| 6,019,745 A | 2/2000 | Gray .......................... 604/131 |
| 6,092,722 A | 7/2000 | Heinrichs et al. |
| 6,126,670 A | 10/2000 | Walker et al. |
| 6,223,633 B1 * | 5/2001 | Chien-Chich ................ 81/438 |
| 6,312,441 B1 | 11/2001 | Deng |
| 6,315,060 B1 * | 11/2001 | Schuda et al. .............. 173/132 |
| 6,604,744 B2 * | 8/2003 | Monge ........................ 279/79 |
| 6,626,862 B1 | 9/2003 | Duchon et al. ............. 604/110 |
| 6,688,611 B2 * | 2/2004 | Gifford et al. ................ 279/71 |
| 6,960,894 B2 | 11/2005 | Carusillo et al. |
| 2003/0093103 A1 | 5/2003 | Malackowski |

FOREIGN PATENT DOCUMENTS

| | | |
|---|---|---|
| EP | 0 630 820 | 12/1994 |
| EP | 0 951 921 | 10/1999 |
| EP | 1 110 504 | 6/2001 |
| JP | 07 178107 | 7/1995 |
| NL | 1001018 | 2/1997 |
| WO | WO 94/10921 | 5/1994 |
| WO | WO 00/24318 | 5/2000 |

OTHER PUBLICATIONS

U.S. Appl. No. 60/395,881, filed Jul. 15, 2002.

* cited by examiner

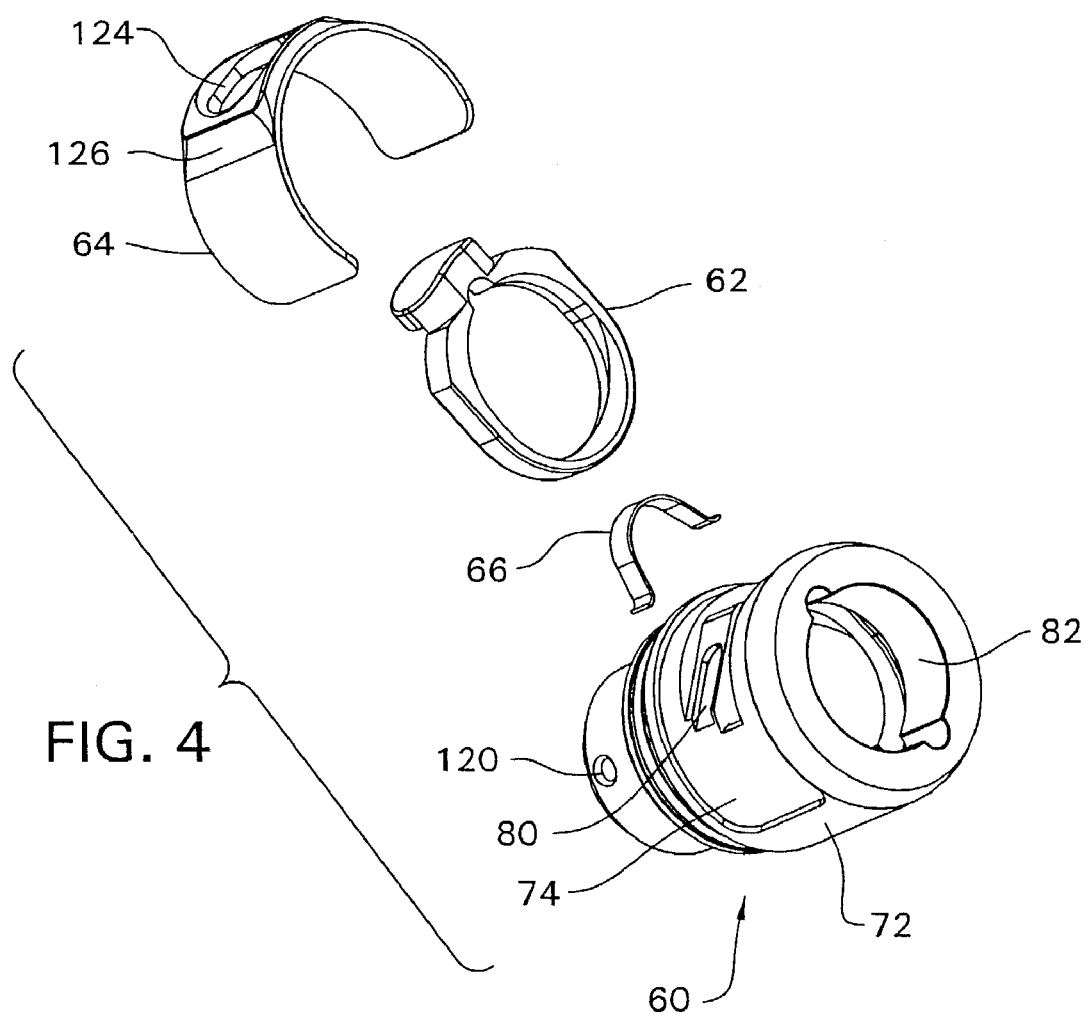

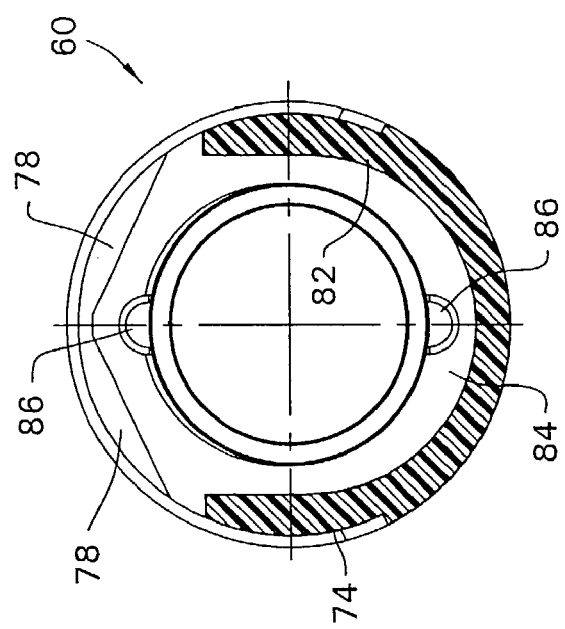
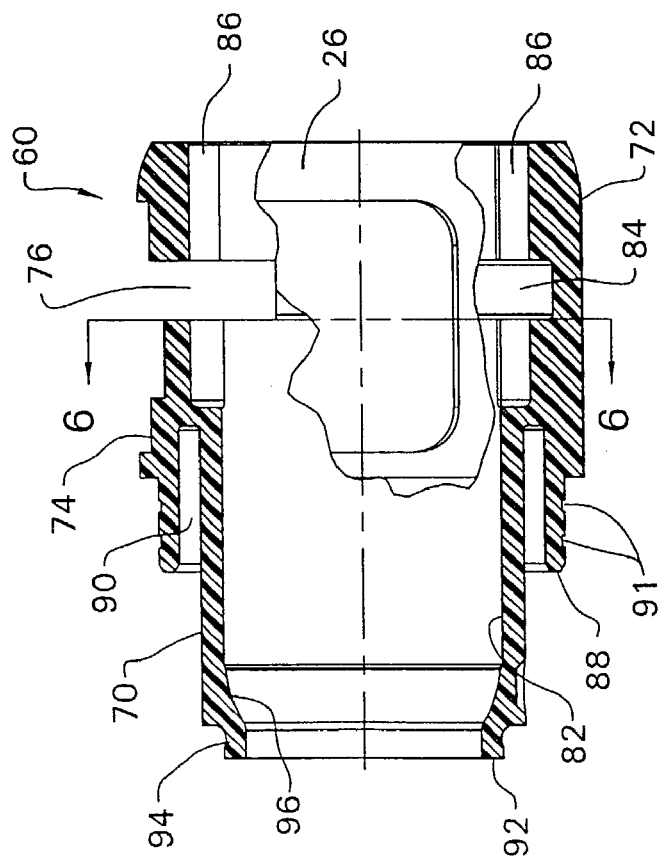

SURGICAL TOOL SYSTEM WITH QUICK RELEASE COUPLING ASSEMBLY

RELATIONSHIP TO EARLIER-FILED APPLICATION

This application is a continuation-in-part of U.S. patent application Ser. No. 10/214,937, filed Aug. 8, 2002, the contents of which are incorporated herein by reference.

FIELD OF THE INVENTION

This invention is related generally to a powered surgical tool system useful for performing endoscopic surgical procedures and, more particularly, to a system with a handpiece and complementary cutting accessory that are constructed to allow the rapid coupling and decoupling of the cutting accessory to the handpiece and that requires relatively few components to assemble.

BACKGROUND OF THE INVENTION

Endoscopic surgical procedures are routinely performed in order to accomplish various surgical tasks. In an endoscopic surgical procedure, small incisions, called portals, are made in the patient. An endoscope, which is a device that allows medical personnel to view the surgical site, is inserted in one of the portals. Surgical instruments used to perform specific surgical tasks are inserted into other portals. The surgeon views the surgical site through the endoscope to determine how to manipulate the surgical instruments in order to accomplish the surgical procedure. An advantage of performing endoscopic surgery is that, since the portions of the body that are cut open are minimized, the portions of the body that need to heal after surgery are likewise reduced. Moreover, during an endoscopic surgical procedure, only relatively small portions of the patient's internal organs and tissue are exposed to the open environment. This minimal opening of the patient's body lessens the extent to which a patient's organs and tissue are open to infection.

The ability to perform endoscopic surgery is enhanced by the development of powered surgical tools especially designed to perform endoscopic surgical procedures. One such tool, for example, is sold by the Applicant's Assignee under the trademark HUMMER II. This tool is in the form of a cylindrical handpiece designed to be held in the hand of the surgeon. Internal to the handpiece there is a motor. A front end of the handpiece is provided with a coupling assembly for releasably holding a cutting accessory. The types of cutting accessories that are attached to these handpieces include edgers, resectors, planers and burrs. Integral with the motor and coupling assembly is a means for transmitting the rotary power developed by the motor to the cutting accessory.

The handpiece also has a suction conduit. This is because, in an endoscopic surgical procedure, irrigating fluid is introduced into the surgical site. This fluid serves as transport media for removing tissue and debris from the surgical site. In order to remove the irrigating fluid, and the material in the fluid, a suction path is provided through the cutting accessory and the handpiece. A suction pump is connected to the handpiece to provide the suction force needed for drawing the fluid and material away from the surgical site. In order to control the suction flow through the cutting accessory and the handpiece, the handpiece is provided with a manually operated valve. Thus, with a single handpiece, a surgeon both manipulates the cutting accessory and controls the suction of material away from the surgical site.

While current endoscopic surgical tool systems have proven useful, there are some disadvantages associated with their construction. Some of these disadvantages are associated with the coupling assemblies integral with the handpieces. For example, many coupling assemblies are provided with release levers that a surgeon or an assistant pivots to place the coupling assembly in a release state wherein a cutting accessory can be removed from the handpiece. Some coupling assemblies are provided with coupling assemblies that not only must be placed in the release state to remove a cutting accessory, but must also be placed in the release state in order to couple a cutting accessory to the handpiece. Requiring medical personnel to perform this step can add to the overall time it takes to remove and replace cutting accessories.

Moreover, often a coupling assembly comprises numerous components. Providing these components and arranging them together to form a functional coupling assembly adds to the overall cost of providing the handpiece to which the coupling assembly is attached. Another disadvantage associated with providing a coupling assembly that has numerous components is that, as with any system, the more components that are provided increases the possibility that, due to the failure of one component, the whole assembly will malfunction. This is especially true when a system is provided with a large number of moving components.

Also, as discussed in application Ser. No. 10/214,937, the Application from which this application claims priority and which is incorporated herein by reference, recently there has been an interest in providing surgical tool systems that allow data to be inductively transferred between the handpiece and the complementary cutting accessory. This system requires the placement of a coil in the distal end, the front end, of the handpiece so that there can be inductive signal transfer between it and a complementary coil in the adjacent proximal end of the associated cutting accessory. This means that, not only must the front end of the handpiece contain the components forming a coupling assembly, it must also have a space in which a coil can be housed. Given the components that comprise some coupling assemblies, the only way both goals can be accomplished is to increase the overall length of the handpiece. This may require lengthening of the proximal end of the complementary cutting accessory, the end fitted in the handpiece. This handpiece lengthening can increase the overall size and weight of the handpiece. These increases run contrary to one goal of modern surgical tool design. This goal being that, to facilitate ease of use of a surgical tool, its size should be kept as small as possible and its weight as low as possible.

SUMMARY OF THE INVENTION

This invention relates generally to a new powered surgical tool system that can be used to perform surgical procedures such as endoscopic surgical procedures. The system of this invention includes a handpiece with a coupling assembly that is relatively easy to assemble. The coupling assembly of this invention also has an easy to operate release button and is further designed so that it does not have to be placed in a release state in order to fit a cutting accessory to the associated handpiece. The coupling assembly of this invention includes a collet in which it is possible to fit a coil in order to facilitate the inductive signal transfer of data between the handpiece and the complementary cutting accessory.

The system of this invention has a cutting accessory with an outer hub and an inner drive hub. The outer hub has an ear with a relatively simple geometry that forms the locking member for holding the accessory to a handpiece. An RFID tag is disposed in the hub. A seal is located around the RFID tag to protect the tag from the ambient environment. The seal is provided with stop tabs. Collectively, the stop tabs and a head section of the drive tube cooperate to hold the drive hub in the outer hub. The seal also is formed with ribs that are located outside the proximal end of the outer hub. The ribs provide a seal between the cutting accessory and the adjacent inner wall to which the cutting accessory is mounted.

BRIEF DESCRIPTION OF THE DRAWINGS

The invention is pointed out with particularity in the claims. The above and further advantages may be better understood by reference to the following description taken in conjunction with the accompanying drawings, in which:

FIG. 4 is an exploded view of the coupling assembly;

FIG. 5 is a longitudinal cross sectional view of the coupling assembly collet;

FIG. 6 is a lateral cross sectional view of the coupling assembly collet taken along line 6—6 of FIG. 5;

DETAILED DESCRIPTION

Figure 1:
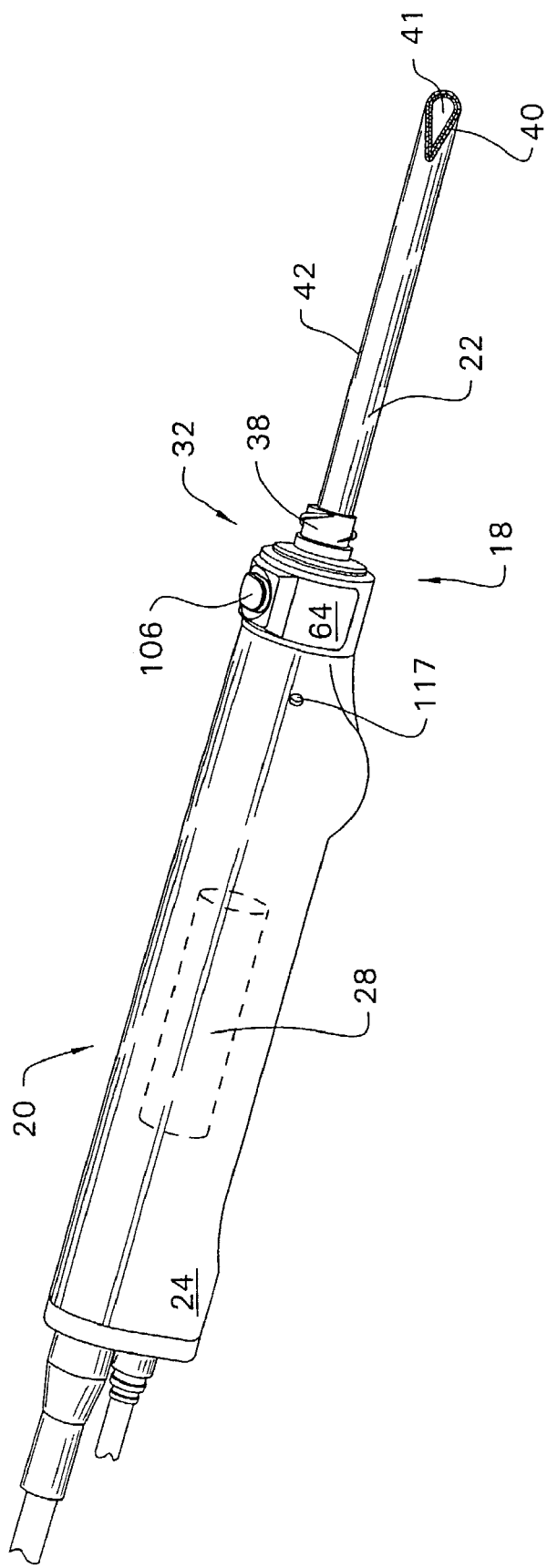
FIG. 1 is a perspective view of an endoscopic surgical handpiece of this invention that depicts a complementary cutting accessory secured to the handpiece.
Figure 2:
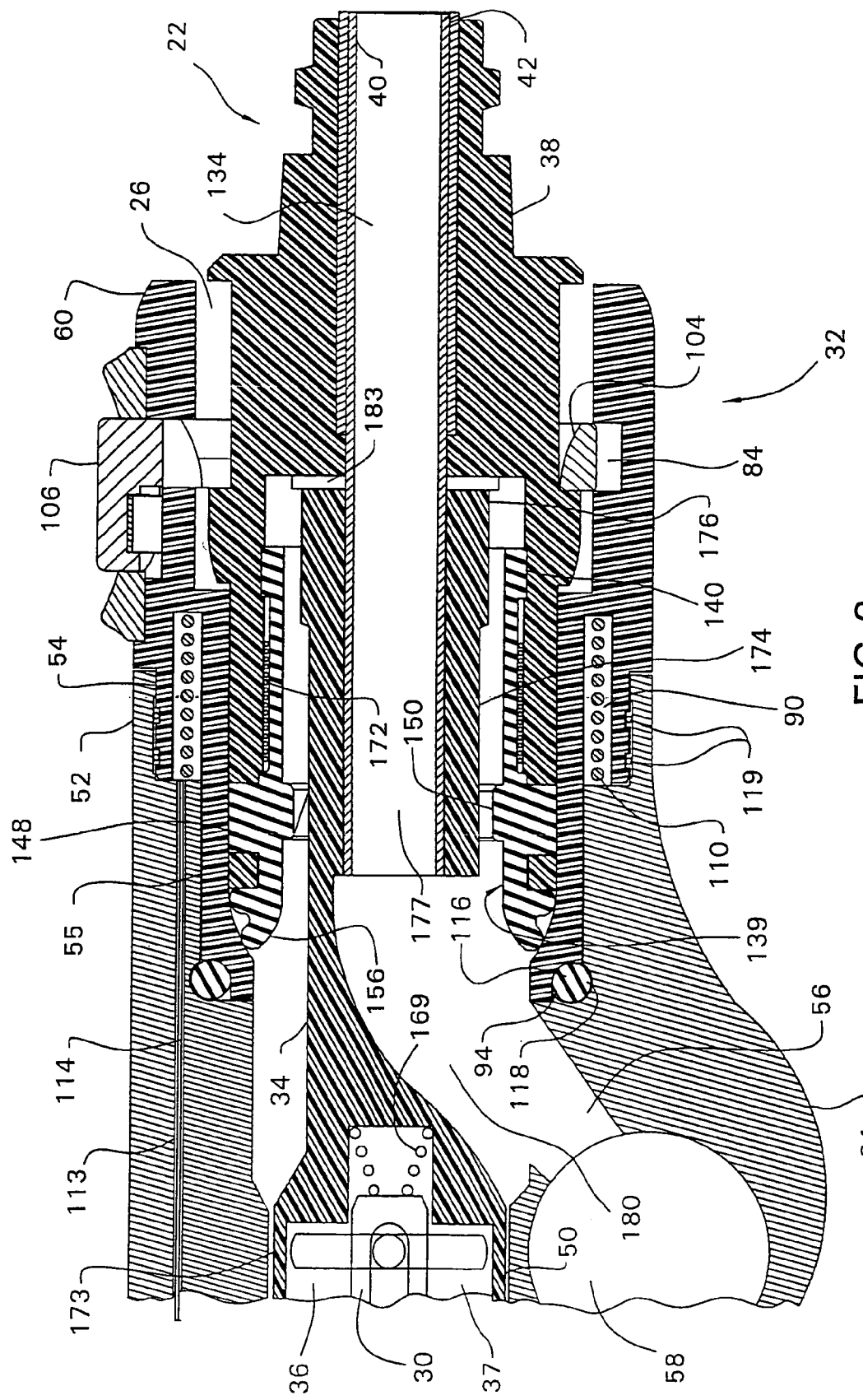
FIG. 2 is a cross sectional view of the distal end of the handpiece to which a cutting accessory is attached.

The surgical tool system 18 of this invention, as seen in FIGS. 1 and 2, includes an endoscopic handpiece 20, sometimes called a surgical tool. A complementary cutting accessory 22 is attached to the handpiece 20. The handpiece 20 includes a generally cylindrical, elongated housing 24. The distal end of the housing 24 is formed with a bore 26 for receiving the proximal end of the cutting accessory 22. (Throughout this document, "distal" is understood to be away from the face of the surgeon holding the handpiece 20; "proximal" is understood to mean towards the face of the surgeon.) A motor 28, depicted in phantom, is disposed inside the housing. A rotating output shaft 30, which is connected to the motor 28 for actuation by the motor, is disposed inside bore 26. A coupling assembly 32 is mounted to the front end of the housing 24 for removably holding the cutting accessory 22 to the handpiece 20.

The cutting accessory 22 includes a drive hub 34 that releasably engages the output shaft 30. For the purposes of this invention, the exact geometry of the output shaft 30 and drive hub 34 that facilitate the releasable engagement of these components is not relevant. By way of example though, in the depicted version of the invention, a drive pin 36 extends through the distal end of motor output shaft 30. The drive hub 34 is formed to have a slot 37 that extends forward from the proximal end of the hub. When the cutting accessory 22 is fitting in handpiece bore 26, the shaft drive pin 36 seats in the drive hub slot 37. The seating of the drive pin 36 in the drive hub slot 37 causes the drive pin to impart the rotation moment of the output shaft to the drive hub.

The cutting accessory 22 includes a static outer hub 38 which surrounds the drive hub 34 that is held in housing bore 26 by the coupling assembly 32. A tubular drive shaft 40 is integrally attached to the drive hub 34 and extends forward, distally from the drive hub 34 through the outer hub 38 and forward from the handpiece 20. A cutting head, such as a burr or open window shaver, shaver illustrated, is attached to or integrally formed with the distal end of the drive shaft 40. A tubular-shaped outer shell 42, sometimes called the outer housing, extends forward from the outer hub 38 and surrounds the drive shaft 40. The extent to which the distal end of the outer shell 42 surrounds the drive shaft 40 cutting head is a function of the design of the particular cutting accessory 22. It should be further understood that the distal end of the drive shaft 40 is provided with an opening 41 through which suction is drawn from the surgical site.

When the surgical tool system 20 of this invention is employed to perform a surgical procedure, irrigating fluid is introduced into the site through the distal end of the cutting accessory. This fluid may be flowed to the site through the annular space between the drive shaft 40 and the inner wall of outer shell 42. Alternatively, the fluid is introduced through a separate cannula that opens into the surgical site. Suction is drawn through the handpiece 20 and drive shaft of the accessory 22 to remove irrigating fluid and the material entrained in the irrigating fluid.

Handpiece housing 24 is formed with an elongated bore 50 that extends axially through the housing. The distal end of bore 50 is located rearwardly from the proximal portion of the bore 26. While not seen in the drawings, it should be understood that bore 50 is the space in which the handpiece motor 28 is seated. The distal end of housing 24 is formed to have a ring shaped head 52 that defines a first counterbore 54 that is coaxial with bore 50. Immediately proximal to head 52, housing 24 has a second counterbore 55 also coaxial with bore 50. Second counterbore 55, which has a diameter between that of bore 50 and the first counterbore 54, is a transition bore between bore 50 and the first counterbore 54. A suction bore 56 branches off of bore 50. Suction is drawn through the cutting accessory drive shaft 40 through the suction bore 56. Partially seen in FIG. 2 is a valve bore 58 that intersects the suction bore 56. A valve (not illustrated), is disposed in the valve bore 58 for regulating the suction flow through the cutting accessory 22 and the handpiece 20.

Figure 3:
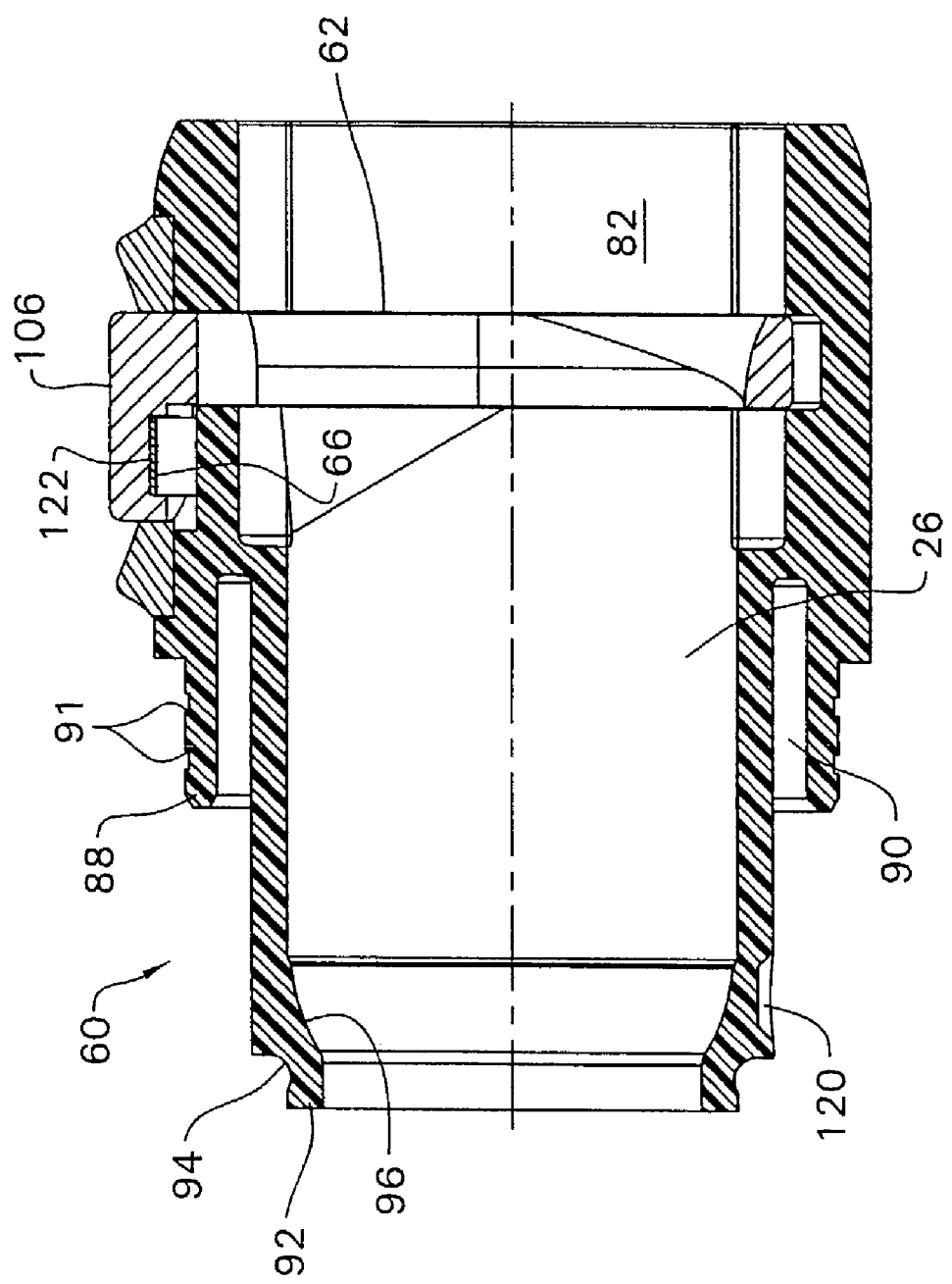
FIG. 3 is a cross sectional view of the components forming the coupling assembly of this invention.

The coupling assembly, now described primarily by reference to FIGS. 2, 3 and 4, is secured to the distal end of the handpiece housing 24. Specifically, the coupling assembly includes a generally ring shaped collet 60 that is secured to the housing 24. Collet 60 is the portion of the handpiece 20 that defines bore 26. A locking ring 62 is movably disposed in the collet 60. A cover plate 64 is fitted over the collet 60 and locking ring 62 so as to hold the locking ring to the collet. A wave spring 66 seated between the collet 60 and the locking ring 62 biases the locking ring into a locked state in which the ring holds the cutting accessory outer hub 38 in handpiece bore 26.

The collet 60, is formed of a plastic able to withstand the rigors of steam sterilization, such as a polyphenylsulfone plastic, one such plastic being sold under the trademark RADEL by Amoco Chemicals/British Petroleum. In some versions of the invention, the plastic forming the collet 60 is 15% to 30% glass filled. The collet 60, as seen in detail in FIGS. 4–6, includes a sleeve-shaped base 70. Extending distally from base 70, the collet 60 has a head 72 that has an outer diameter greater than the outer diameter of the base 70. Bore 26 extends axially through collet 60, from the distal end of head 72 to the proximal end of base 70. Collet 60 is further formed so that head 72, has an arcuate-shaped recessed section 74 that surrounds between 190° and 250° of the outer circumference of the collet. In more preferred versions of the invention, recessed section 74 surrounds between 230° and 240° of the outer circumference of head 72. Within recessed section 74, collet head 72 is further shaped to have a laterally extending slot 76 that opens into bore 26. Immediately proximal to slot 76, the collet head 72 is shaped so as to have two small flat surfaces 78 that angle away from an apex that is parallel with the longitudinal axis of the collet 60. Collet head 72 is further formed so that within each flat surface 78 there is a groove 80 with a flat base surface recessed from the associated flat surface 78.

Collet 60 is formed so that within head 72 and the adjacent distal section of base 70 there is an inner wall 82 with a constant diameter circular cross-sectional profile that defines the distal portion of bore 26. Within head 72, collet 60 is further formed so that there is an arcuate groove 84 that extends inwardly of wall 82, away from the center axis of the collet. Groove 84 is diametrically opposite the arcuate section of collet head 72 inscribed by slot 76. Collet 60 is further shaped to have two diametrically opposed slots 86 that extend proximally away from the distal end opening of head 72 and terminate immediately forward of the proximal end of the head. Slots 86 are diametrically opposed from each other. A first one of the slots 86 intersects slot 76; the opposed slot 86 intersects groove 84. It should be understood that groove 84 has a depth greater than that of the intersecting slot 86. As will be understood hereinafter, the greater depth of groove 84 is designed to provide space so that the adjacent section of the locking ring 62 can extend into the portion of groove 84 located below the intersecting slot 86.

Collet 60 is further formed to have a skirt 88 that extends proximally from the proximal end of head 72 and circumferentially surrounds the adjacent distal end of base 70. More particularly, it will be noted that skirt 88 is spaced away from the outer surface of the portion of the base surrounded by the skirt so as to define an annular space 90 between these two components of the collet 60. Skirt 88 is shaped so that around its outer surface there are two spaced apart, circumferentially extending grooves 91.

The collet 60 is shaped so that the portion of base 70 that extends rearwardly from head 72 has both a generally constant outer diameter and wall thickness. The proximal end of the base 70 has an annular tail section 92 that is stepped inwardly from the more distal portions of the base. More particularly, there is a stepped surface 94 along the outside of the base between the distal portions and tail section 92 that has a curved cross-sectional profile. Also, collet 60 is shaped so that inside base 70, immediately distal to tail section 92, there is an inner wall section 96, immediately distal to wall 82, with an inwardly curved profile.

Figure 7:
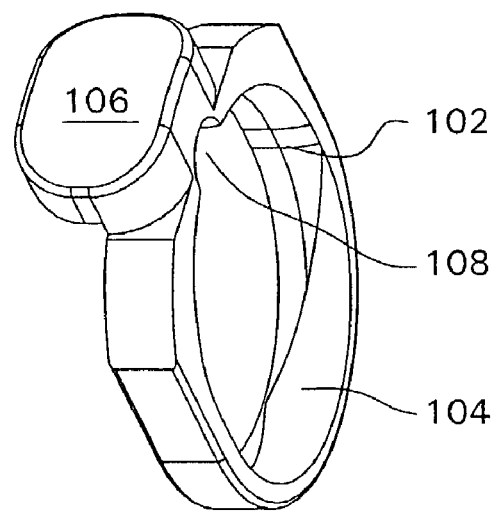
FIG. 7 is a perspective view of the locking ring and release button.
Figure 8:
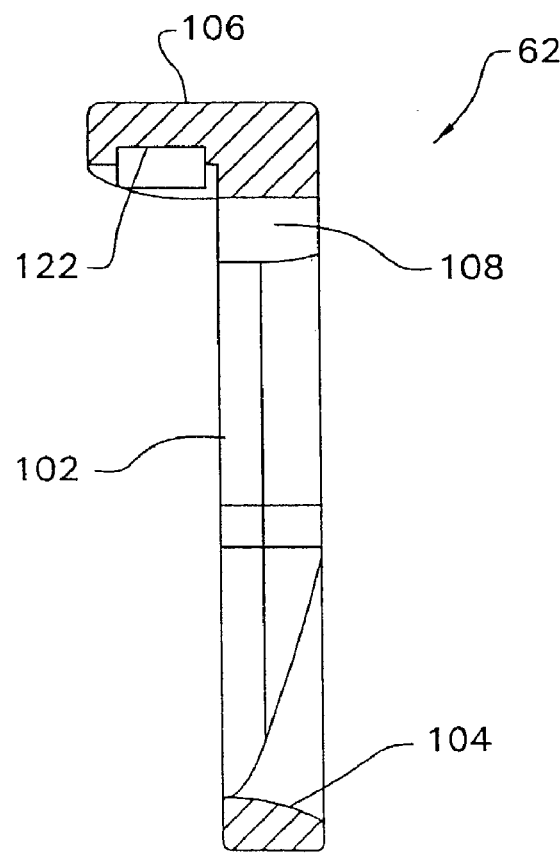
FIG. 8 is a cross sectional view of the locking ring and release button.

Locking ring 62 is formed of a sterilizable metal, such as stainless steel. The locking ring 62, now described by reference to FIGS. 4, 7 and 8, is shaped to define a center opening 102 with a shape that is oval. Locking ring 62 is further formed to have a lip 104 that projects into opening 102 from one of the curved ends of the ring. Lip 104 provides the end of the ring 62 with which it is integral a taper such that the overall wall thickness of the ring increases along a line that extends proximally away from the distal-facing side of the ring.

A release button 106 is integrally formed with the locking ring 62 so as to be located on the side of the ring opposite the side with which lip 104 is integral. More specifically, release button 106 both subtends the end of the ring to which the button is mounted and extends proximally away from the ring. A slot 108 is formed in the portion of the ring 62 to which release button 106 is attached. Slot 108 opens into center opening 102 and has the same cross-sectional profile as the slots 86 formed in collet 60.

Figure 12:
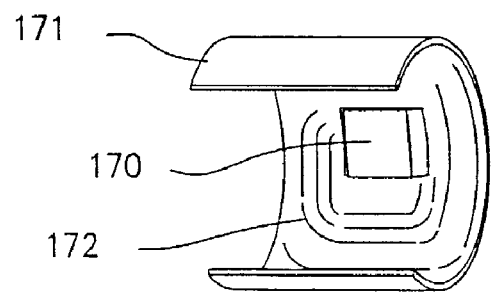
FIG. 12 is a perspective view of the cutting accessory tag assembly.

As part of the assembly of handpiece 20 of this invention, collet 60 is attached to handpiece housing 24. Specifically, the collet base 60 seats in the second counterbore 55, as seen in FIG. 2. Prior to the attachment of the collet to the handpiece housing 24, a coil 110 is seated in annular space 90. The coil, which may be a wire wrap or a conductive trace formed on a flexible substrate, is the coil used to facilitate inductive signal transfer to/from a radio frequency identification device (RFID) chip 170 disposed in the accessory outer hub 38 (FIG. 12). Coil 110 is connected to downline signal processing components through conductors 114 that extend through a longitudinally extending bore 113 formed in the handpiece housing 24.

An O-ring 116 extends around the collet base tail section 92. O-ring 116 abuts the stepped surface of housing 24 that defines the transition from bore 50 to second counterbore 55. More particularly, the stepped surface of housing 24 is formed to define a groove 118 with an arcuate profile in which O-ring 116 seats. The inner portion of O-ring 116 is seated against the curved collet step surface 94.

Collet 60 is secured to handpiece housing 24, in part, by an adhesive capable of withstanding the rigors of sterilization, such as a silicone adhesive. The adhesive is placed between the opposed surface of housing head 52 and collet skirt 88. A fraction of the adhesive collects in the grooves 91 that extend around the outer surface of skirt 88. Upon the curing of the adhesive in the grooves, the adhesive forms two O-rings 119 between the housing 24 and the collet 60. The O-rings 119 prevent fluid flow from the ambient environment moving through the handpiece-collet interface.

Removable set screws, not illustrated, further hold the collet 60 to the distal end of the housing 24. These set screws extend through threaded bores 119 formed in the distal end of the handpiece housing 24, (one bore shown in FIG. 1). The ends of the set screws set in recesses 120 formed in the outer surface of collet base 70, (one recess shown in FIG. 4).

Locking ring 62 is slip-fitted in collet slot 76. More particularly, the locking ring 62 is attached to the collet 60 so that the end of the ring with which lip 104 is integral seats in groove 84. When the locking ring 62 is fitted to the collet 60, the release button extends rearwardly, over flat surfaces 78 and the adjacent portion of the recessed section 74.

The wave spring 66 is disposed between the collet head 72 and the release button 106. Specifically, each end of the wave spring 66 is seated in a separate one of the grooves 80 formed in the collet head 72. The topmost crest portion of the wave spring is fitted against a recessed surface 122 formed in the release button 106 immediately proximal to locking ring 62.

Cover plate 64 is snap-secured in the recess 74 formed in the collet head. The cover plate 64 has an arcuate shape corresponding to that of the collet recess 74. There is an opening 124 in the center of the place through which release button 106 extends. In the illustrated version of the invention, the cover plate 64 has a center section 126 with greater wall thickness than that of the surrounding ends. Opening 124 is formed in the center section 126.

Figure 9:
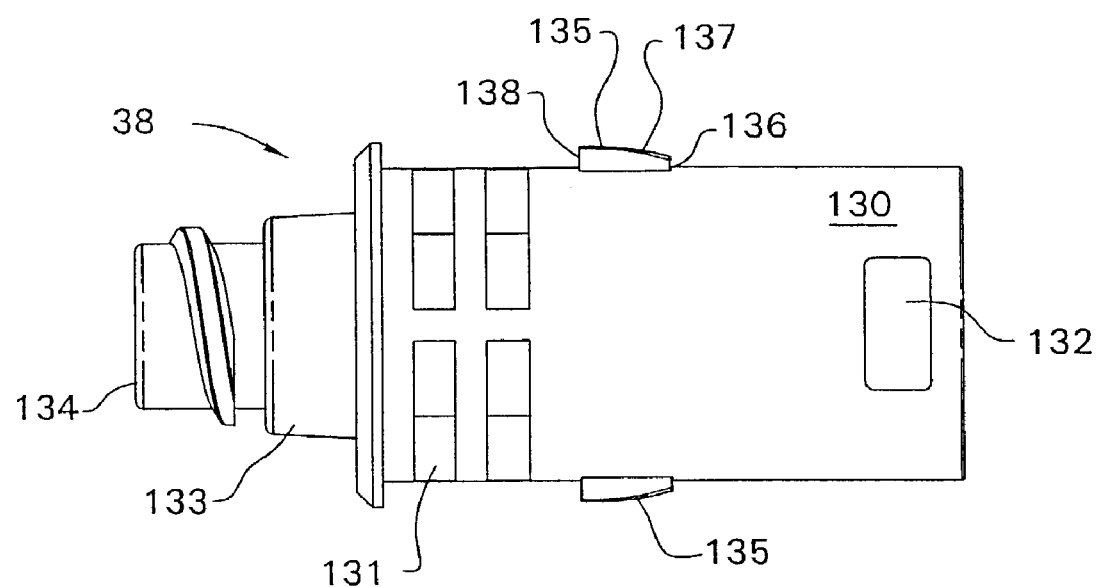
FIG. 9 is a plan view of the hub of the cutting accessory of this invention.
Figure 10:
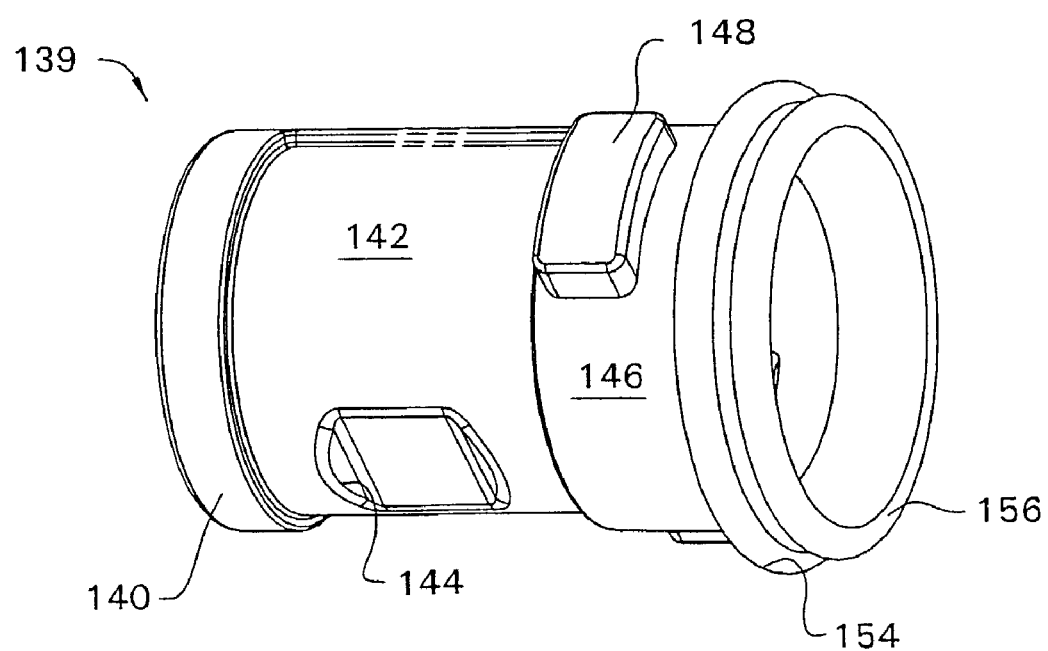
FIG. 10 is a perspective view of the coil seal of the cutting accessory.
Figure 11:
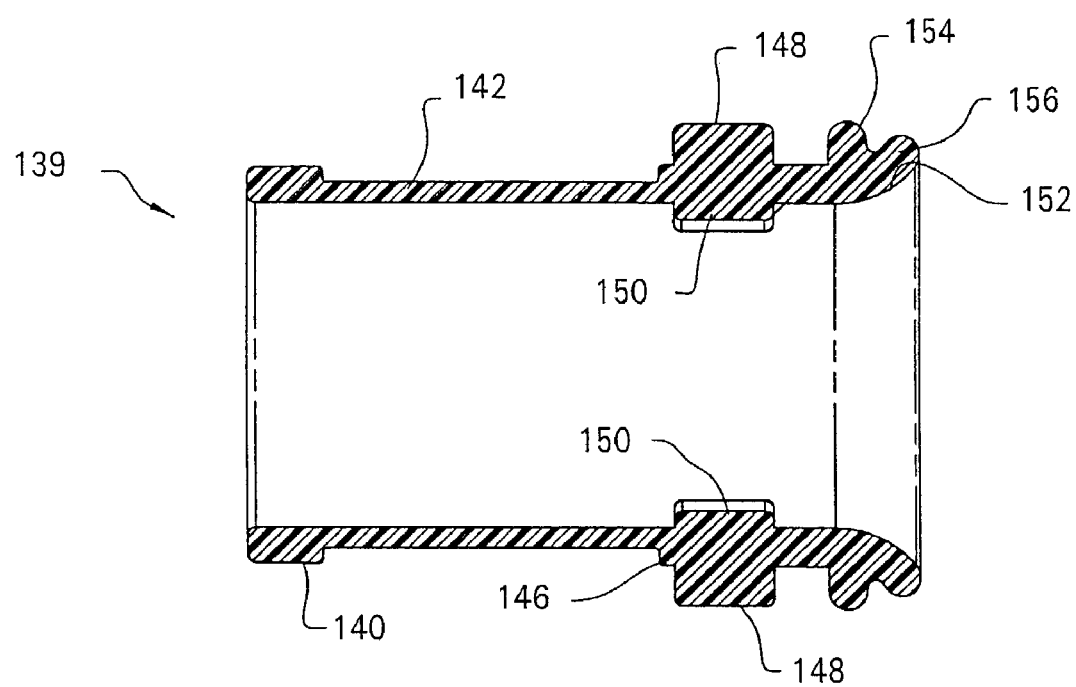
FIG. 11 is a cross-sectional view of the coil seal of the cutting accessory.

The static outer hub 38, which is formed of rigid plastic, is now described by reference to FIGS. 9, 10 and 11. The outer hub 38 is constructed to have a sleeve-shaped base 130. The base 130, it will be observed, is formed with two diametrically opposed, generally rectangularly shaped openings 132. Extending forward from base 130 and formed integrally therewith is a substantially solid head 133. While head 133 is substantially solid, the outer hub 38 is formed so that a bore 134 extends axially through the head. Outer shell 42 is mounted in bore 134 in any conventional manner to extend forward from head 133. In the depicted version of the invention, the outer surface of hub head 133 is provided with threading, not identified. The threading is provided to facilitate the releasable screw securement of the cutting accessory 22 to a cannula fitted in the portal formed in the patient and directed towards the surgical site.

Outer hub 38 is further formed to have two diametrically opposed ears 135 that are integrally formed with, and extend outwardly from, the base 130. Each ear 135 is formed so as to have a relatively short proximally-directed face 136 that extends laterally away from the longitudinal axis of the hub 38. Distal to face 136, each ear 135 has a parallel distally directed face 138. A side surface 137 extends between the opposed faces 136 and 138 of ear 135. Each ear is formed such that the side surface 137 has a rise or taper at least adjacent the proximally-directed faces 136 such that overall thickness of the ear 135 increases moving away from face 136. In some versions of the invention, the ears 135 are formed so that side surfaces 137 have a profile that, extending from the proximally-directed faces 136 is curved or arcuate.

In the depicted version of the invention, laterally extending grooves 131 are formed in the distal end of the outer hub base 130. The grooves 131 extend circumferentially around the base. Two longitudinally offset, parallel sets of grooves 131 are shown. Each set of grooves consists of a set of spaced apart grooves. Grooves 131 are provided to reduce the overall amount of material required to provide the outer hub 38 and to facilitate the injection molding of the outer hub.

A generally tube-shaped coil seal 139 is disposed in hub base 130. Coil seal 139 is formed from flexible sterilizable material. In one version of the invention, coil seal 139 is formed from a silicon rubber that has 55 Shore A durometer hardness. The coil seal 139 is shaped to have a first end section, distal end section 140, that has a constant outer diameter and inner diameter. Extending proximally from the distal end section 140, the coil seal 139 has a main section 142. Main section 142 has the same inner diameter as distal end section 140 and a narrower outer diameter. The coil seal 139 is further formed to define a generally rectangular recess 144 in the outer surface of main section 142. Located proximal to main section 142, the coil seal 139 has a second end section, proximal end section 146. The inner and outer diameters of proximal end section 146 are the same as those of the distal end section 140. The proximal end section 146 of the coil seal 139 is further formed to have two diametrically opposed lock tabs 148. Each lock tab 148 extends radially outwardly from the outer surface of the locking section 146. The locking section also has two diametrically opposed stop tabs 150 that extend inwardly from the inner wall of the lock section. In the depicted version of the invention, each stop tab 150 is radially aligned with a separate one of the lock tabs 148.

Coil seal 139 is further formed to have a tail section 152 that extends rearwardly from the locking section and that forms the proximal end of the seal. The tail section 152 is formed to define two annular spaced apart ribs 154 and 156 that extend circumferentially around coil seal 139. Both ribs 154 and 156 extend beyond the outer diameter of the seal locking section 146. In the depicted version of the invention, the diameter of the circle subtended by the more proximal of the two ribs, rib 156, is less than the diameter subtended by the other rib, rib 154. Tail section 152 is further formed to have an inner wall that is outwardly flared.

When a cutting accessory 22 of this version of the invention is assembled, an RFID chip 170, seen in FIG. 12, is seated in seal recess 144. A coil 172 connected to the chip 170 is disposed over the reduced diameter outer surface of seal main section 142. In the version of the invention depicted in FIG. 12, the. chip 170 is mounted on a small flex circuit 171; the coil 172 is a conductive trace formed on the flex circuit 171. After manufacture of the flex circuit 171, the flex circuit, with the chip 170 mounted thereon, is wrapped in cylinder over seal main section 142 so that the chip seats in recess 144.

The RFID chip-coil-and-seal assembly is fitted in hub base 130. Consequently, both the RFID chip 170 and coil 172 are disposed between the inner wall of the hub base and the outer surface of coil seal 139. Owing to the relative dimensions of outer hub 38 and coil seal 139, the outer surfaces of the seal's distal end and proximal end sections 140 and 146, respectively, press against the inner wall of the hub base 130. This contact forms a seal around chip 170 and coil 172. Thus, in most preferred versions of the invention, there is no need to employ an adhesive or other chemical to provide a moisture barrier around the chip 170 and coil 172.

As part of the insertion of the coil seal 139 into the outer hub 38, lock tabs 148 are seated in hub base openings 132. The seating of the lock tabs 148 in openings 132 holds the coil seal 139 to the outer hub 38. When the coil seal 139 is so attached to outer hub 38, tail section ribs 154 and 156 are located proximal to the proximal end opening of the hub.

As described above, the drive hub 34, now described by reference to FIG. 2, transfers the rotary motion of the handpiece output shaft 30 to the cutting accessory drive shaft 40. The drive hub has a stem 173 that is the proximal end portion of the drive hub. Stem 173 is the portion of the drive hub 34 that is formed with the geometric features that facilitate the coupling of the hub to the motor output shaft 30. Located within the base of the bore within stem 173 there is a coil spring 169 with a conical profile.

Extending forward from stem 173, the drive hub 34 has a neck 174 that extends into the proximal end opening of the outer hub 38. In the depicted version of the invention, neck 174 has a diameter less than that of stem 173. A head 176 located forward of the neck 174 forms the distal end of the drive hub 34. Head 176, it will be observed, has a larger diameter than the adjacent neck 174. More specifically, the drive hub 34 is formed so that neck 174 has a diameter less than that of the open section defined by the inner surfaces of coil seal stop tabs 150. In contrast, drive hub head 176 has a diameter that is slightly greater than the opening defined by the coil seal stop tabs 150. For example, in one version of the invention, the neck 174 of the drive hub 34 has an outer diameter of 0.31 inches and head 176 has a diameter of 0.344 inches. In this version of the invention, the open section of the bore defined by the coil seal tabs 150 once the coil seal 139 is seated in the outer hub 38 and slightly compressed is between 0.33 and 0.34 inches.

A bore 177 extends from the distally directed front face of the drive hub head 176, through head 176 and partially through neck 174. The proximal end of the drive shaft 40 is secured in the distal portion of bore 177 by any conventional means. The drive hub 34 is further formed to have a suction port 180 on one side of the neck 174 that curves into, and is in fluid communication with, the proximal end of bore 177. Suction port 180 is the opening in the drive hub 34 through which suction is drawn.

The cutting accessory 22 is assembled by inserting the drive shaft 40 through the outer hub 38 and into the outer shell 42. When the cutting accessory 22 is so assembled, the drive hub and drive shaft subassembly are moved past coil seal 139 in hub bore 134. Owing to the dimensioning of the components, the drive coupler head 176 abuts the coil seal stop tabs 150. Owing to the compressibility of the material from which the coil seal 139 is formed, a small amount of force compresses the stop tabs 150 to allow the complete insertion of the drive coupler and rotating shaft. After assembly, if the cutting accessory 22 is held vertically, the drive hub head 176 will drop so as to abut stop tabs 150. Thus, the stop tabs 150 prevent gravity, without any additional force, from causing the drive hub 34 and drive shaft 40 to drop out of outer hub 38.

In the depicted version of the invention, a washer 183 is shown surrounding the portion of the drive shaft 40 located immediately forward of the drive hub 34. Washer 183 is thus sandwiched between the distally-directed face of the drive hub 34, and the adjacent proximally directed recessed face of the outer hub 38. Washer 183 is provided with some cutting accessories 22, such as burs, as both a spacer and to reduce the friction contact between the drive and outer hubs 34 and 38, respectively.

The cutting accessory 22 is secured to the handpiece 20 by inserting the drive and outer hubs 34 and 38, respectively, into the open end of collet bore 73. The outer hub ears 135 are inserted in collet slots 86. As the outer hub 34 is seated in opening 26, the arcuate side surface 137 of the ear 135 adjacent the locking ring lip 104 presses against the lip. Owing to the complementary tapers of lip 104 and the adjacent ear 135, the movement overcomes the force of wave spring 66 that urges that lip into the slot 86. Thus, the lip 104, and the adjoining arcuate section of the locking ring 62 are pressed into collet groove 84 so that the ear 135 can pass over the lip.

Once the outer hub ear 135 passes over the locking ring lip 104, the wave spring 66 urges the lip back into the position in which the lip is within the portion of groove 84 that intersects the contiguous slot 86. When the locking ring 62 is so seated, lip 104 abuts the distally-directed face 138 of the ear 135 to hold the outer hub 38 and the whole of the cutting accessory 22 to the handpiece 20. When the coupling assembly 32 is in this state, the assembly is considered in the locked state.

While not part of this invention, it should be understood that, owing to the geometry of the proximal end of the drive hub 34, the seating of the cutting accessory 22 in opening 26 causes the drive hub 34 to engage the motor output shaft 30. When the drive hub 34 is so seated, the narrow diameter end of spring 169 presses against the distal facing face of the motor output shaft 37. Spring 169 thus pushes the drive hub 34 forward.

When the cutting accessory 22 is fitted in the handpiece opening 26, ribs 154 and 156 abut the tapered inner wall section 96 of collet base 70. Ribs 154 and 156 thus function as a seal that prevents leakage from the suction channel to the outside environment.

As a result of the coupling of the cutting accessory 22 to the handpiece 20, accessory coil 172 is disposed in the space surrounded by handpiece coil 110. The coils 110 and 172 are thus in close enough proximity to each other so that there is inductive coupling of signals between the coils.

During the course of a surgical procedure, a surgeon may want to replace the cutting accessory 22 attached to the handpiece 20 with a different cutting accessory. The installed cutting accessory is removed by the downward depression of the release button 106. This action causes a like downward movement of the locking ring 62 so that lip 104 retracts into the portion of groove 84 below the contiguous slot 86. As a result of this motion, lip 104 moves clear of the adjacent outer hub ear 135. Once the locking ring 62 is so positioned, the coupling assembly 32 is referred to as being in the release state. The transition of the coupling assembly 32 to the release state allows the spring 169, which is previously compressed, to expand. Since the distal end of the spring 169 is disposed against the drive hub 34, the spring pushes the drive hub 34, and therefore the outer hub 38, a short distance forward of the open end of bore 26. Consequently, it becomes a simple task to manually pull the cutting accessory 22 from the handpiece 20.

Once the cutting accessory 22 is extracted from the bore 26 so that the outer hub ear 135 clears the locking ring 62, the pressure on the handpiece can be released without adversely effecting the removal of the cutting accessory. The replacement cutting accessory 22 is then inserted into the handpiece 20. As with the insertion of the first cutting accessory 22, there is no need for the medical personnel to depress the release button 106 in order to secure the new accessory to the handpiece 20.

The coupling assembly 32 of this invention is constructed out of just a few components. Only two of the components, the locking ring 62 and the wave spring 66, move. Thus, given the relatively small number of components incorporated into this coupling assembly, and the fact that only two of the components move, it is relatively economic both to provide the parts of this assembly and to put them together to manufacture the completed assembly.

The coupling assembly 32 of this invention is further constructed so that it does not have to be placed into the release mode in order for the assembly to lock a cutting accessory 22 to the handpiece 20 with which the assembly is integral. Collectively, the handpiece 20 and complementary cutting accessory 22 are arranged so that either of the outer hub ears 135 can seat in either of the collet slots 86. Thus, during the process of fitting the cutting accessory 22 to the handpiece 20, the accessory does not need to be rotated more than 180° before the accessory is properly aligned to be inserted into the handpiece opening 26. Both of these features of the invention make it possible for surgical personnel to rapidly fit a cutting accessory to the handpiece with relatively little manipulation or concentration.

Also, the collet 60 of the described version of the invention is formed from plastic. Thus, since the collet 60 is non-metallic, the collet can readily serve as a housing for coil 110 and not adversely affect the inductive signal transfer between coils 110 and 112. Also, the material from which the collet 60 is formed is lighter in weight than the aluminum from which the handpiece housing 24 is formed. Thus, by providing a plastic collet, the overall weight of the coupling assembly, and the handpiece 20 to which it is installed, is minimized. The minimization of handpiece weight serves to lessen the fatigue to which a surgeon is exposed as a result of having to hold and manipulate the handpiece for an extended period of time.

Still another feature of this invention is that the inner wall section 96 of collet 60, the surface of the collet against which ribs 154 and 156 abut is curved. Consequently, as soon as there is forward movement of the drive hub 34 out of bore 26, the surface contact between the ribs 154 and 156 and the collet 60 is broken. The breaking of this contact means causes a like break in the friction bond that would otherwise hold the ribs 154 and 156 to the collet. The breaking of this bond means that the kinetic force released by the continued expansion of spring 169 is not applied to overcoming friction bond. Instead this spring force serves to urge the hubs 34 and 38 of bore 26.

Another feature of the coupling assembly 32 of this invention is that it houses coil 110. Thus, in a relatively short overall section of the handpiece, in a section usually less than 1.7 inches or less in length and, more particularly, 1.4 or less inches in length, the handpiece of this invention has both a coupling assembly and a coil that is employed to read and write data into a RFID chip 170 fitted in the cutting accessory 22.

Moreover, the locking members that are integral with the cutting accessory 22 of this invention, ears 135, are, from a manufacturing standpoint, relatively easy to provide. It is a relatively simple task to form the ears 135 during the molding of the outer hub 38.

Coil seal 139 of the cutting accessory 22 performs a number of different functions. Specifically, the seal serves as one of the components that protects the RFID chip 170 and coil 172 from the ambient environment. Ribs 154 and 156 of the seal function as a seal around the drive hub 34. This seal ensures that the suction drawn through the handpiece causes fluid flow from the distal end of the drive shaft 40, not the surrounding environment. Stop tabs 150, in combination with the relatively large diameter of the drive hub head 176, cooperate to prevent the drive hub and drive shaft sub assembly from falling out of the outer hub and outer shell subassembly.

It should be recognized that the foregoing was a description of one preferred version of the invention and that other versions of the invention may vary from what has been described. For example, while generally the surgical handpiece 20 and complementary cutting accessory that form the system of this invention are designed to perform endoscopic surgery, use of the invention is not so limited. The components of the system of this invention can also be employed to perform other types of surgical procedures.

Also, some versions of the invention may not include all features of the described version of the invention. For example, some systems of this invention may not have the coils that are employed to facilitate inductive signal transfer between the handpiece and complementary cutting accessory. In some of these versions of the invention, it may therefore not be necessary to provide the collet as a component separate from the handpiece housing. In these versions of the invention, the locking ring, the wave spring and the cover plate are fitted directly onto the handpiece housing or body. An advantage of this arrangement of the invention is that it even further reduces the number of components that need to be provided in order to construct the handpiece of this invention.

Similarly, there may be reasons to provide a tool system of this invention with some or all of the features of the coil seal but not to employ the specifically disclosed means for releasably holding the outer hub to the handpiece. Thus, an alternative version of the invention may comprise an elastomeric member attached to the proximal end of the hub that includes one or more of the described ribs. This version of the invention may be constructed if the cutting accessory is not provided with an RFID chip. In these versions of the invention, the ribs of these members perform the sealing function of described ribs 154 and 156. In these versions of the invention, the outer hub is provided with surface features different from the described ears to facilitate the releasable attachment of the cutting accessory to the handpiece.

With regard to the ribs 154 and 156, it should similarly be recognized that their number are exemplary, not limiting. Some versions of the invention may be provided with a single rib, some versions three or more ribs. Also, in the described version of the invention the rib 156 is seated is of smaller outer diameter than rib 154. This is because the section of the inner wall of the housing against which rib 156 is of smaller diameter than the section against which rib 154 abuts. In alternative versions of the invention, the diameters of these ribs may vary to compensate for like differences in the profiles of the surfaces the ribs are intended to abut.

Further, it should be recognized that the location of the coil seal lock tabs 148 and the complementary outer hub openings in which the lock tabs are seated may be different from what has been described. Thus, the lock tabs may be integral with the distal end section 140 of the seal. Also, both the end sections of the seal may, in some versions of the invention, be provided with lock tabs. In these versions of the invention it should be understood that the outer hub is formed with longitudinally spaced openings in which the lock tabs are seated.

It should similarly be recognized that the geometry and number of the stop tabs 150 may vary from what has been described. For example, in some versions of the invention, instead of providing two tabs, the stop member may be a ring formed of flexible material. The ring thus defines an open section of the outer hub base proximal end opening that has a diameter greater than that of drive hub neck 174 and less than that of the drive hub head 176. This ring may or may not be provided with slots to facilitate its flexing in order to allow the insertion of the drive hub head into the outer hub proximal end opening. Alternatively, three or more tabs formed of flexible, compressible or otherwise yielding material may be provided as stop tabs.

Also, the number of ears 135 integral with the cutting accessory outer hub 38 may be different from what has been described. In some versions of the invention, it may be desirable to provide a single ear 135. This version of the invention may be provided when there is a need to position the cutting accessory in a specific rotational orientation relative to the handpiece 20. In other versions of the invention, it may be desirable to provide the cutting accessory with three or more ears. In these versions of the invention, the collet and locking ring are appropriately shaped to accommodate the seating of the ears that do not abut the lock ring. An advantage of these versions of the invention is that they further reduce the extent to which the cutting accessory 22 needs to be rotated in order to position one ear in the slot 86 where the locking ring will then block the movement of the ear.

Also, alternative constructions of the coupling assembly may be possible. For example, in some versions of the invention, the wave spring and release button may be on opposite sides of the locking ring. In these versions of the invention, the lip portion of the locking ring, the portion that blocks movement of the outer hub 38 is located adjacent the wave spring. The spring biases the locking ring so that the lip is normally in the locked state. The release button is depressed to retract the lip into an adjacent slot in the collet so as to place the locking ring in the release state.

Similarly, the biasing member that holds the locking ring in the locked state may have different forms than what has been described. For example, not all spring versions of this biasing member need be wave springs. In some versions of the invention, a coil spring or leaf spring may perform this function. Also, this biasing member need not always be a metal or plastic spring. In alternative versions of the invention, elastomeric material disposed between a static component integral with the handpiece housing and the locking ring may serve as the member that releasably holds the locking ring in the locked state.

It should likewise be understood that the geometry of the components of this invention may vary from what has been described. For example, there is no requirement that the accessory outer hub and complementary handpiece opening in which the hub is inserted always have a circular profile. In other versions of the invention, it may be desirable that these components have an oval profile or in the form of a polygon, for example, a square or pentagonal shape. Similarly, the ears of the outer hub, which function as its lock tabs, may have a geometry different from what has been described. For example, there may be a reason to provide the longitudinally extending surfaces of these components with linear profiles.

Also, it should be recognized that not all versions of this invention incorporate a motor as the power generating unit. In some versions of the invention, the power generating unit may consist of a device that generates ultrasonic energy, RF energy, thermal energy or photonic, light, energy. In these versions of the invention, the coupling member that transfers the power generated by the power generating unit to the cutting accessory will be different from what has been described. The coupling member may also be different if the power generating unit is the previously described motor 28. For example, sometimes the motor output shaft 30 may not be provided with a drive pin. In these versions of the invention, teeth integral with the output shaft function as the coupling member and engage with complementary teeth on the accessory drive hub to transfer the motive power from the motor to the cutting accessory.

Therefore, it is an object of the appended claims to cover all such variations and modifications as come within the true spirit and scope of this invention.

What is claimed is:

1. A powered surgical handpiece comprising:
   a housing having a distal end defining a non-rotatable accessory coupling arrangement, said distal end having an accessory opening dimensioned to receive a proximal end of a cutting accessory, a lock slot contiguous with the accessory opening dimensioned to receive a lock tab that extends outwardly from the proximal end of the cutting accessory, and a groove that intersects the lock slot and opens into the accessory opening;
   a power generating unit disposed within said housing for actuating the cutting accessory, said power generating unit including a coupling member for transferring power generated by said power generating unit to the cutting accessory;
   a lock ring fitted in the distal end of said housing so as to surround the accessory opening and the lock slot, the groove accommodating a section of said lock ring that is disposed in the lock slot, wherein the groove and the lock slot each have a depth, the depth of the groove being greater than the depth of the lock slot, said lock ring and said distal end of said housing collectively dimensioned so that when said lock ring is moved to the release state, said lock ring seats in a portion of the groove below the lock slot;
   a release button integral with said lock ring that is depressed to move said lock ring from the locked state to a release state in which said lock ring is clear of the lock slot;
   a biasing member disposed between an outer surface of the distal end of said housing and said lock ring or said release button so as to bias said lock ring so that the release button is urged away from said distal end of said housing to hold said lock ring in a locked state wherein a section of said lock ring is disposed in the lock slot; and
   a cover plate fitted over said lock ring and secured to said distal end of said housing to hold said lock ring thereto.

2. The powered surgical handpiece of claim 1, wherein said housing includes a body and a collet that is attached to an end of said body to define the distal end of said housing.

3. A powered surgical handpiece comprising:
   a housing having a distal end with an accessory opening dimensioned to receive a proximal end of a cutting accessory and a lock slot continguous with the accessory opening dimensioned to receive a first lock tab that extends outwardly from the proximal end of the cutting accessory, said housing including an auxiliary slot separate from the lock slot that opens into the accessory opening for receiving a second lock tab that extends outwardly from the proximal end of the cutting accessory;
   a power generating unit disposed within said housing for actuating the cutting accessory, said power generating unit including a coupling member for transferring power generated by said power generating unit to the cutting accessory;
   a lock ring movably fitted in the distal end of said housing so as to surround the accessory opening and the lock slot;
   a biasing member disposed between said housing and said lock ring for holding said lock ring in a locked state wherein a section of said lock ring is disposed in the lock slot; and
   a release button integral with said lock ring that is depressed to move said lock ring from the locked state to a release state in which said lock ring is clear of the lock slot.

4. The powered surgical handpiece of claim 3, wherein said lock ring is shaped to define an auxiliary indentation that at least partially subtends the area subtended by the auxiliary slot.

5. The powered surgical handpiece of claim 3, wherein:
   said biasing member extends between an outer surface of said housing and said lock ring or said release button so as to bias said lock ring so that the release button is urged away from said housing; and
   a cover plate is fitted over said lock ring and secured to said housing to hold said lock ring to said housing.

6. The powered surgical handpiece of claim 3, wherein:
   said housing includes a body and a collet that is attached to an end of said body to form the distal end of said housing, said collet being formed to define the accessory opening and the lock slot; and said lock ring is movably secured to said collet and said biasing member extends between said collet and said lock ring.

7. The powered surgical handpiece of claim 3, wherein said power generating unit is a motor, said motor having an output shaft that extends into the opening and the coupling member is integral with said output shaft.

8. A powered surgical handpiece comprising:
a housing having a distal end defining a non-rotatable accessory coupling arrangement, said distal end having an accessory opening dimensioned to receive a proximal end of a cutting accessory and a lock slot contiguous with the accessory opening dimensioned to receive a lock tab that extends outwardly from the proximal end of the cutting accessory;
a power generating unit disposed within said housing for actuating the cutting accessory, said power generating unit comprising a motor, said motor having an output shaft that extends into the opening, and a coupling member integral with said output shaft for transferring power generated by said power generating unit to the cutting accessory;
a lock ring fitted in the distal end of said housing so as to surround the accessory opening and the lock slot;
a biasing member disposed between the distal end of said housing and said lock ring for holding said lock ring in a locked state wherein a section of said lock ring is disposed in the lock slot; and
a release button integral with said lock ring that is depressed to move said lock ring from the locked state to a release state in which said lock ring is clear of the lock slot.

9. A powered surgical tool comprising:
a handpiece housing having a distal end and an accessory opening that extends inwardly from the distal end and that is dimensioned to receive an outer hub of a cutting accessory;
a collet attached to an end of said housing to form the distal end of said housing, said collet being formed to define a distal section of the accessory opening and a lock slot, said collet comprising: a base disposed in said housing, a head that extends forward from said base and defines the distal end of said housing, and a skirt that extends from said head in surrounding relation with said base and is spaced away therefrom so as to define an annular space around said base;
a coil disposed in said collet within the annular space defined by said base and said skirt of said housing;
a motor disposed in said handpiece housing, said motor having a rotating output shaft and a coupling member attached to said output shaft for releasably coupling a drive hub of the cutting accessory to said output shaft so that said output shaft and said drive hub rotate in unison;
a coupling assembly attached to said handpiece housing for releasably and non-rotably securing the outer hub of the cutting accessory to said handpiece housing, said coupling assembly comprising:
the lock slot defined in said collet extending longitudinally inwardly from the distal end of said housing and contiguous with the accessory opening, the lock slot being dimensioned to receive a lock tab that extends from an outer surface of the outer hub;
a lock ring movably secured to said collet, said lock ring positioned to surround the accessory opening and the lock slot, said lock ring positioned to selectively intersect the lock slot;
a biasing member extending between said collet and said lock ring for urging said lock ring into a locked state in which a section of said lock ring intersects the lock slot; and
a release button integral with said lock ring that is depressed to move said lock ring from the locked state to a release state wherein said lock ring is spaced from the lock slot.

10. The powered surgical tool of claim 9, wherein:
said handpiece housing is formed with a groove that opens into the accessory opening, the groove being positioned to intersect the lock slot, wherein the groove and the lock slot each have a depth, the depth of the groove being greater than the depth of the lock slot; and
said lock ring and said handpiece housing are collectively dimensioned so that when said lock ring is moved to the release state, said lock ring seats in a portion of the groove below the lock slot.

11. The powered surgical tool of claim 9, wherein said coupling assembly is formed so that said lock slot and said release button are located opposite each other.

12. A powered surgical tool comprising:
a handpiece having a distal end and an accessory opening that extends inwardly from the distal end that is dimensioned to receive an outer hub of a cutting accessory;
a motor disposed in said handpiece, said motor having a rotating output shaft and a coupling member attached to said output shaft for releasably coupling a drive hub of the cutting accessory to said output shaft so that said output shaft and said drive hub rotate in unison;
a coupling assembly attached to said handpiece for releasably holding the outer hub of the cutting accessory to said handpiece, said coupling assembly comprising:
a lock slot defined in said handpiece that extends longitudinally inwardly from the distal end thereof and that is contiguous with the accessory opening, the lock slot being dimensioned to receive a first lock tab that extends from an outer surface of the outer hub;
an auxiliary slot formed in said handpiece and being separate from the lock slot and opening into the accessory opening for receiving a second lock tab that extends outwardly from the outer hub of the cutting accessory;
a lock ring mounted to said handpiece, said lock ring being positioned to surround the accessory opening and the lock slot, said lock ring being movably mounted to said handpiece and positioned to selectively intersect the lock slot, said lock ring being shaped to define an auxiliary indentation that at least partially subtends the area subtended by the auxiliary slot;
a biasing member disposed between said handpiece and said lock ring for urging said lock ring into a locked state in which a section of said lock ring intersects the lock slot; and
a release button integral with said lock ring that is depressed to move said lock ring from the locked state to a release state wherein said lock ring is spaced from the lock slot.

13. The powered surgical tool of claim 12, wherein said coupling assembly is formed so that said lock slot and said release button are located opposite each other.

14. The powered surgical tool of claim 12, wherein:
said handpiece includes a housing and a collet that is attached to an end of said housing to form the distal end thereof, said collet being formed to define a distal section of the accessory opening and the lock slot; and said lock ring is movably secured to said collet and said biasing member extends between said collet and said lock ring.

15. A powered surgical handpiece comprising:

a housing having a distal end with an accessory opening dimensioned to receive the proximal end of a cutting accessory and a lock slot contiguous with the accessory opening dimensioned to receive a lock tab that extends outwardly from a proximal end of the cutting accessory;

a power generating unit disposed within said housing for actuating the cutting accessory, said power generating unit including a coupling member for transferring power generated by said power generating unit to the cutting accessory;

a lock ring disposed in the distal end of said housing so as to surround the accessory opening and the lock slot;

a biasing member disposed between said housing and said lock ring for holding said lock ring in a locked state wherein a section of said lock ring is disposed in the lock slot; and a release button connected to said lock ring that is depressed to move said lock ring from the locked state to a release state in which said lock ring is clear of the lock slot, said lock ring being configured to receive and lock the cutting accessory to said housing without depressing of the release button.

16. The powered surgical handpiece of claim 15, wherein said lock ring includes a lip having a tapered face so that contact with a tapered face of the lock tab enables movement of the accessory to overcome the force of the biasing member to enable the handpiece to receive the cutting accessory without depressing of the release button.

17. The powered surgical handpiece of claim 15, wherein:

said handpiece is formed with a groove that opens into the accessory opening, the groove intersecting the lock slot and being positioned to accommodate the section of said lock ring that is disposed in the lock slot, wherein the groove and the lock slot each have a depth, the depth of the groove being greater than the depth of the lock slot; and said lock ring and said handpiece are collectively dimensioned so that when said lock ring is moved to the release state, said lock ring seats in a portion of the groove below the lock slot.

18. The powered surgical handpiece of claim 15, wherein said handpiece is further formed to have an auxiliary slot separate from the lock slot that opens into the accessory opening for receiving a second lock tab that extends outwardly from the proximal end of the cutting accessory.

19. The powered surgical handpiece of claim 15, wherein:

said biasing member extends between a surface of said housing and said lock ring or said release button so as to bias said lock ring and said housing so that the release button is urged away from said housing; and a cover plate is fitted over said lock ring and secured to said housing to hold said lock ring to said housing.

20. The powered surgical handpiece of claim 15, wherein:

said housing includes a body and a collet that is attached to an end of said body to form the distal end of said housing, said collet being formed to define the accessory opening and the lock slot; and said lock ring is movably secured to said collet and said biasing member extends between said collet and said lock ring.

21. The powered surgical handpiece of claim 15, wherein said power generating unit is a motor, said motor having an output shaft that extends into the opening and the coupling member is integral with said output shaft.

22. A powered surgical handpiece comprising:

a housing having a distal end with an accessory opening dimensioned to receive the proximal end of a cutting accessory and a lock slot contiguous with the accessory opening dimensioned to receive a first lock tab that extends outwardly from the proximal end of the cutting accessory;

a power generating unit disposed within said housing for actuating the cutting accessory, said power generating unit including a coupling member for transferring power generated by said power generating unit to the cutting accessory;

a lock ring slidably fitted in the distal end of said housing so as to surround the accessory opening and the lock slot;

a release button associated with said lock ring; and a biasing member disposed between an outer face of said housing and said release button to hold said lock ring in a locked state wherein a section of said lock ring is disposed in the lock slot, wherein the release button is depressed to move said lock ring from the locked state to a release state in which said lock ring is clear of the lock slot.

23. The powered surgical handpiece of claim 22, wherein:

said handpiece is formed with a groove that opens into the accessory opening, the groove intersecting the lock slot and being positioned to accommodate the section of said lock ring that is disposed in the lock slot, wherein the groove and the lock slot each have a depth, the depth of the groove being greater than the depth of the lock slot; and said lock ring and said handpiece are collectively dimensioned so that when said lock ring is moved to the release state, said lock ring seats in a portion of the groove below the lock slot.

24. The powered surgical handpiece of claim 22, wherein said handpiece is further formed to have an auxiliary slot separate from the lock slot that opens into the accessory opening for receiving a second lock tab that extends outwardly from the proximal end of the cutting accessory.

25. The powered surgical handpiece of claim 22, wherein:

said biasing member urges the release button away from said housing; and a cover plate is fitted over said lock ring and secured to said housing to hold said lock ring to said housing.

26. The powered surgical handpiece of claim 22, wherein:

said housing includes a body and a collet that is attached to an end of said body to form the distal end of said housing, said collet being formed to define the accessory opening with the lock slot; and said lock ring is slidably secured to said collet and said biasing member extends between said collet and said lock ring.

27. The powered surgical handpiece of claim 22, wherein said power generating unit is a motor, said motor having an output shaft that extends into the opening and the coupling member is integral with said output shaft.

* * * * *